(12) United States Patent
Axelrod et al.

(10) Patent No.: US 11,357,416 B2
(45) Date of Patent: Jun. 14, 2022

(54) ADAPTIVE TUNING FOR VOLUME CLAMP BLOOD PRESSURE MEASUREMENT

(71) Applicant: Edwards Lifesciences Corporation, Irvine, CA (US)

(72) Inventors: Blake W. Axelrod, Sierra Madre, CA (US); Alexander H. Siemons, Yorba Linda, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 666 days.

(21) Appl. No.: 16/266,366

(22) Filed: Feb. 4, 2019

(65) Prior Publication Data

US 2019/0261872 A1 Aug. 29, 2019

Related U.S. Application Data

(60) Provisional application No. 62/635,857, filed on Feb. 27, 2018.

(51) Int. Cl.
*A61B 5/0225* (2006.01)
*A61B 5/00* (2006.01)
(Continued)

(52) U.S. Cl.
CPC ........ *A61B 5/02255* (2013.01); *A61B 5/0261* (2013.01); *A61B 5/02241* (2013.01); *A61B 5/6843* (2013.01)

(58) Field of Classification Search
CPC . A61B 5/0225; A61B 5/02241; A61B 5/6843; A61B 5/02255; A61B 5/0261; A61B 5/022–02255; A61B 5/02416
See application file for complete search history.

(56) References Cited

U.S. PATENT DOCUMENTS 4,510,940 A * 4/1985 Wesseling .......... A61B 5/02255 600/480
4,524,777 A * 6/1985 Kisioka .............. A61B 5/02255 600/490
(Continued)

FOREIGN PATENT DOCUMENTS

EP 2198773 A1 6/2010

OTHER PUBLICATIONS

Boehmer, R.D., "Continuous, real-time, noninvasive monitor of blood pressure: Penaz methodology applied to the finger.," J Clin Monit. Oct. 1987;3(4):282-7.
(Continued)

*Primary Examiner* — Oommen Jacob
(74) *Attorney, Agent, or Firm* — Eric T. King; Womble Bond Dickinson (57) ABSTRACT

Disclosed is a system to provide adaptive tuning through a control system to a finger cuff connectable to a patient's finger to be used in measuring the patient's blood pressure in the patient's artery by a blood pressure measurement system utilizing a volume clamp method. When the finger cuff is placed around the patient's finger, the bladder and the LED-PD pair aid in measuring the patient's blood pressure by the blood pressure measurement system utilizing the volume clamp method, wherein the adaptive tuning system: applies a first pressure impulse and measures a pleth versus time response; from the pressure versus time response, determines pleth servo gains that compensate for delays in a pleth response of the finger; and uses the determined pleth servo gains in the control system in measuring the patient's blood pressure by the blood pressure measurement system utilizing the volume clamp method.

22 Claims, 10 Drawing Sheets (51) Int. Cl.
*A61B 5/026* (2006.01)
*A61B 5/022* (2006.01)

(56) References Cited

U.S. PATENT DOCUMENTS

| | | | | |
|---|---|---|---|---|
| 4,539,997 | A * | 9/1985 | Wesseling | A61B 5/02141 600/490 |
| 4,869,261 | A | 9/1989 | Penaz | |
| 5,152,296 | A | 10/1992 | Simons | |
| 5,533,511 | A * | 7/1996 | Kaspari | A61B 5/02007 600/494 |
| 6,616,613 | B1 | 9/2003 | Goodman | |
| 6,632,181 | B2 * | 10/2003 | Flaherty | A61B 5/02133 600/480 |
| 6,699,199 | B2 | 3/2004 | Asada et al. | |
| 7,625,285 | B2 | 12/2009 | Breving | |
| 8,343,062 | B2 * | 1/2013 | Fortin | A61B 5/02241 600/490 |
| 8,814,800 | B2 * | 8/2014 | Fortin | A61B 5/022 600/490 |
| 2006/0195034 | A1 * | 8/2006 | Skrabal | A61B 5/6806 600/490 |
| 2007/0004977 | A1 * | 1/2007 | Norris | A61B 5/7203 600/336 |
| 2008/0103375 | A1 * | 5/2008 | Kiani | A61B 5/14551 600/323 |
| 2010/0298717 | A1 | 11/2010 | Parfyonov et al. | |
| 2011/0105918 | A1 * | 5/2011 | Fortin | A61B 5/0059 600/493 |
| 2019/0261872 | A1 * | 8/2019 | Axelrod | A61B 5/02241 |

OTHER PUBLICATIONS

Finapres® NOVA Technology, "Finapres Medical Systems B.V. offers equipment with proven and advanced technology. Finapres systems are built on combinations of four technologies." Finapres Medical Systems B.V., Retrieved Jul. 11, 2017 http://www.finapres.com/Products/Finpares-NOVA-Technology.

Nogawa, M. et al., "Adaptive control with self-tuning for non-invasive beat-by-beat blood pressure measurement," Conf Proc IEEE Eng Med Biol Soc. 2011;2011:4344-7. doi: 10.1109/IEMBS.2011.6091078.

* cited by examiner

ADAPTIVE TUNING FOR VOLUME CLAMP BLOOD PRESSURE MEASUREMENT

CROSS-REFERENCE TO RELATED APPLICATIONS

This application claims the benefit of U.S. Provisional Patent Application No. 62/635,857, filed Feb. 27, 2018, which is incorporated by reference herein in its entirety.

BACKGROUND

Field

Embodiments of the invention relate to non-invasive blood pressure measurement utilizing the volume clamp method.

Relevant Background

Volume clamping is a technique for non-invasively measuring blood pressure whereby pressure is applied to a patient's finger in such a manner that arterial pressure is balanced by a time varying pressure to maintain a constant arterial volume. In a properly fitted and calibrated system, the applied time varying pressure is equal to the arterial blood pressure in the finger. The applied time varying pressure can be measured thus providing a reading of the patient's arterial blood pressure.

A volume clamp system may contain a pressure generating and regulating system in closed loop feedback with a measurement of the arterial volume. To accurately measure blood pressure, the feedback loop should have sufficient pressure generating and releasing capabilities to match the pressure dynamics of the patient's blood pressure. A high fidelity pressure regulating feedback loop is necessary for accurate blood pressure measurements by the volume clamp technique.

A common technique for measuring the arterial volume is to pass an optical signal at a frequency that is absorbed by blood laterally through the finger. Light is typically generated by an LED (Light-Emitting Diode) on one side of the finger and light that is not absorbed by the finger is measured by a PD (Photodiode) on the other side of the finger. There are two primary arteries that flow in parallel through each finger. As the volume of these two arteries increases with each heartbeat, the amount of light absorbed by the blood in the finger increases and the light measured by the PD decreases. Thus, an optical signal that is inversely proportional to the arterial volume is created. This optical signal is called the plethysmograph, or pleth signal.

A volume clamp system applies pressure to the finger to maintain a constant arterial volume. The mechanical response of the finger arteries to forces applied to the finger (i.e., the finger mechanical responsivity) varies widely depending upon patient physiology and finger size. Furthermore the amount of light absorbed by the finger tissues varies widely depending upon patient physiology, skin pigment, red cell blood count and finger size. A successful volume clamp system should be able to accept a wide range of plethysmograph signals and finger mechanical responsivities.

However, a high fidelity pressure regulating feedback loop is contradictory to a system that is able to accept a wide range of plethysmograph signals and finger mechanical responsivities.

A conventional technique for increasing the fidelity of the volume clamp method involves adjusting the LED intensity to a minimum and the PD amplifier gain to a maximum. This is sub-optimal because it amplifies noise in the pleth signal. Another known technique involves continually self-tuning control loops, in which the error signal is measured dynamically while the system is operational. This is sub-optimal because the magnitude of fluctuations of the error signal are reduced during closed-loop operation. Furthermore, error signal measurement during closed-loop operation couples the effects of the controller and plant transfer functions, complicating the analysis of changes in finger properties.

SUMMARY

Embodiments of the invention may relate to a system to provide adaptive tuning through a control system to a finger cuff connectable to a patient's finger to be used in measuring the patient's blood pressure in the patient's artery by a blood pressure measurement system utilizing a volume clamp method (e.g. to provide for high fidelity). The finger cuff may comprise: a light emitting diode (LED) and photodiode (PD) to form an LED-PD pair to perform measurements of a pleth signal in the patient's artery in the volume clamp method implemented by the blood pressure measurement system; and a bladder connected to a pump and a valve or orifice to apply and release pressure to the patient's finger and the patient's artery, wherein, when the finger cuff is placed around the patient's finger, the bladder and the LED-PD pair aid in measuring the patient's blood pressure by the blood pressure measurement system utilizing the volume clamp method.

The control system may operate in three distinct modes: 1) "open loop," wherein a drive signal drives the pump and valve to pressurize the bladder, resulting in changes in pressure and pleth signals that may be measured and used to adjust gains used in the two closed loop modes; 2) "(closed-loop) pressure servo," wherein, appropriate drive signal(s) are sent to the pump and valve to maintain a predetermined pressure value in the bladder, and the pleth signal may be measured in the closed-loop pressure servo mode and used to adjust gains in the closed loop pleth servo mode; and 3) "(closed-loop) pleth servo," wherein, appropriate drive signal(s) are sent to the pump and valve to affect pressure changes in the cuff that maintain a predetermined pleth signal value, and the pressure signal may be measured and used to determine the patient's blood pressure. The adaptive tuning system may tune the pressure servo (e.g., finding the optimal gains for the pressure servo mode) by operating in the open loop mode to apply a pressure impulse and measure a pressure versus time response, and from the pressure versus time response, determine optimal gains that can be used in the pressure servo mode to compensate for delays in a pressure response of the bladder. The adaptive tuning system may tune the pleth servo (e.g., finding the optimal gains for the pleth servo mode) by operating in the open loop mode to apply a pressure impulse and measure a pleth versus time response, and from the pleth versus time response, determine optimal gains that can be used in the pleth servo mode to compensate for delays in a pleth response of the bladder-finger system. The adaptive tuning system may also tune the pleth servo by operating in the closed-loop pressure servo mode to apply a pressure impulse of a predetermined magnitude and measure a pleth versus time response, and from the pleth versus time response, determine optimal gains that can be used in the pleth servo mode to compensate for delays in a pleth response of the bladder-finger system.

The gains in the pleth servo mode are adjusted to the determined optimal values to measure the patient's blood pressure by the blood pressure measurement system with a high fidelity utilizing the volume clamp method.

DETAILED DESCRIPTION

Embodiments of the invention may relate to a system to provide adaptive tuning through a control system to a finger cuff connectable to a patient's finger to be used in measuring the patient's blood pressure in the patient's artery by a blood pressure measurement system utilizing a volume clamp method (e.g. to provide for high fidelity). The finger cuff may comprise: a light emitting diode (LED) and photodiode (PD) to form an LED-PD pair to perform measurements of a pleth signal in the patient's artery in the volume clamp method implemented by the blood pressure measurement system; and a bladder connected to a pump and a valve or orifice to apply and release pressure to the patient's finger and the patient's artery, wherein, when the finger cuff is placed around the patient's finger, the bladder and the LED-PD pair aid in measuring the patient's blood pressure by the blood pressure measurement system utilizing the volume clamp method.

The control system may operate in three distinct modes: 1) "open loop," wherein a drive signal drives the pump and valve to pressurize the bladder, resulting in changes in pressure and pleth signals that may be measured and used to adjust gains used in the two closed loop modes; 2) "closed-loop) pressure servo," wherein, appropriate drive signal(s) are sent to the pump and valve to maintain a predetermined pressure value in the bladder, and the pleth signal may be measured in the closed-loop pressure servo mode and used to adjust gains in the closed loop pleth servo mode; and 3) "(closed-loop) pleth servo," wherein, appropriate drive signal(s) are sent to the pump and valve to affect pressure changes in the cuff that maintain a predetermined pleth signal value, and the pressure signal may be measured and used to determine the patient's blood pressure. The adaptive tuning system may tune the pressure servo (e.g., finding the optimal gains for the pressure servo mode) by operating in the open loop mode to apply a pressure impulse and measure a pressure versus time response, and from the pressure versus time response, determine optimal gains that can be used in the pressure servo mode to compensate for delays in a pressure response of the bladder. The adaptive tuning system may tune the pleth servo (e.g., finding the optimal gains for the pleth servo mode) by operating in the open loop mode to apply a pressure impulse and measure a pleth versus time response, and from the pleth versus time response, determine optimal gains that can be used in the pleth servo mode to compensate for delays in a pleth response of the bladder-finger system. The adaptive tuning system may also tune the pleth servo by operating in the closed-loop pressure servo mode to apply a pressure impulse of a predetermined magnitude and measure a pleth versus time response, and from the pleth versus time response, determine optimal gains that can be used in the pleth servo mode to compensate for delays in a pleth response of the bladder-finger system. The gains in the pleth servo mode are adjusted to the determined optimal values to measure the patient's blood pressure by the blood pressure measurement system with a high fidelity utilizing the volume clamp method. Hereinafter, gains usable in the pressure servo mode may be referred to as pressure servo gains, and gains usable in the pleth servo mode may be referred to as pleth servo gains.

One embodiment of the invention relates to adaptive self-tuning of control system gains to optimize performance of the volume clamp system. Pressure servo gains may be self-tuned immediately after power-on, and pleth servo gains may be self-tuned with step pressure inputs that are applied periodically during operation. The periodic self-tuning of the pleth servo gains allows the volume clamp system to accommodate signal level fluctuations resulting from physiological changes within the patient's finger, electro-optical changes associated with LED brightness and PD amplification gain, and mechanical changes associated with the interaction between the volume clamp cuff and the patient's finger. Hereinafter the terms self-tuning and auto-tuning may be used interchangeably.

Figure 1:
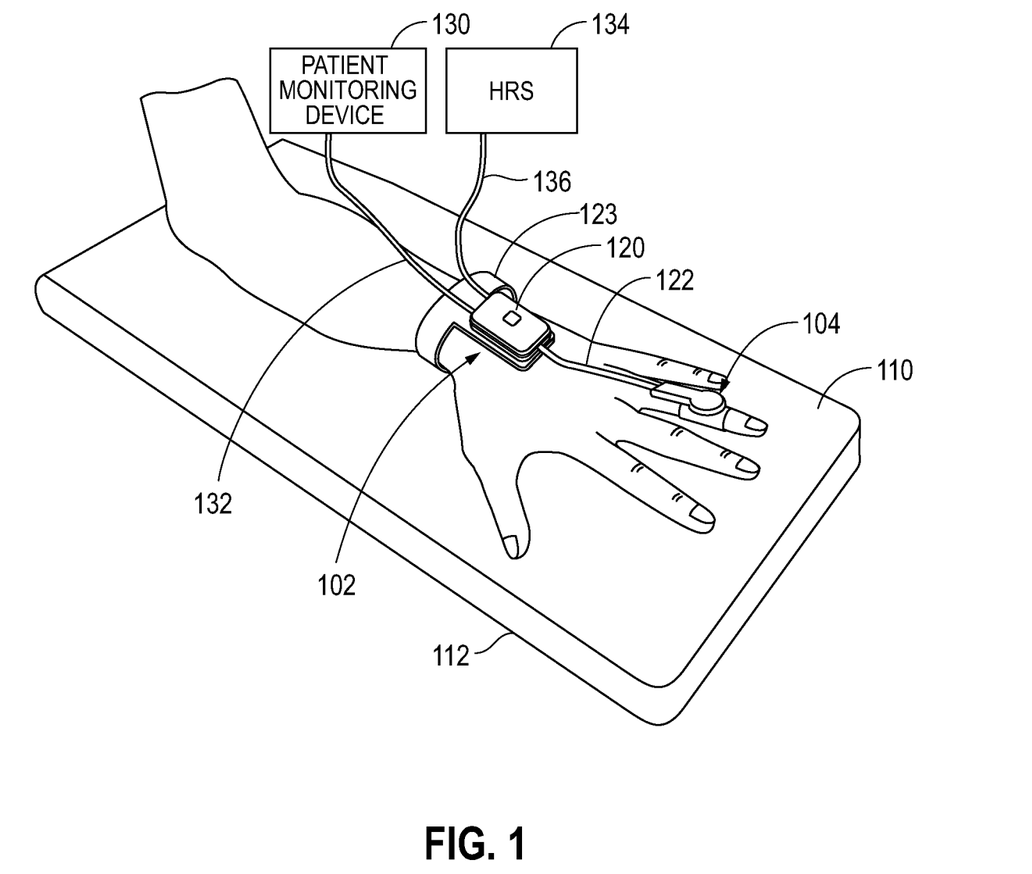
FIG. 1 is a diagram of an example of a blood pressure measurement device, according to one embodiment of the invention.

With reference to FIG. 1, an example of a blood pressure measurement device 102 will be described. The blood pressure measurement device 102 may make measurements using the volume clamp method. As shown in FIG. 1, the blood pressure measurement device 102 may include a finger cuff 104 having a suitable housing and a suitable finger connector (e.g., including a bladder) that may be attached to a patient's finger and a blood pressure measurement controller 120 that may be attached to the patient's body (e.g., a patient's hand). The blood pressure measurement device 102 may further be connected to a patient monitoring device 130 and a heart reference sensor (HRS) 134. The operations of the blood pressure measurement device 102 including the finger cuff 104 and the blood pressure measurement controller 120 will be hereafter described in more detail.

Continuing with this example, as shown in FIG. 1, a patient's hand may be placed on the face 110 of an arm rest 112 for measuring a patient's blood pressure with the blood pressure measurement device 102. As will be described, the blood pressure measurement controller 120 of the blood pressure measurement device 102 may be coupled to a bladder of the finger cuff 104 through a finger cuff connector 122 in order to provide pneumatic pressure to the bladder for use in blood pressure measurement. Blood pressure measurement controller 120 may be coupled to the patient monitoring device 130 through a power/data cable 132 and to the HRS 134 through a HRS connector 136. The patient monitoring device 130 may be any type of medical electronic device that may read, collect, process, display, etc., physiological readings/data of a patient including blood pressure, as well as any other suitable physiological patient readings. Accordingly, power/data cable may transmit data to and from patient monitoring device 130 and also may provide power from the patient monitoring device 130 to the blood pressure measurement controller 120 and finger cuff 104. The HRS 134 may be placed near the patient's heart level and connected by the HRS connector 136 to the blood pressure measurement controller 120 of the blood pressure measurement device 102 to allow for the compensation of potential errors due to differences in height between the finger cuff 104 and the heart level in the calculation of blood pressure measurements.

As can be seen in FIG. 1, in one example, the finger cuff 104 may be attached to a patient's finger and the blood pressure measurement controller 120 may be attached on the patient's hand with an attachment bracelet 123 that wraps around the patient's wrist. However, it should be appreciated that the placement of various components of the blood pressure measurement device 102 described above is illustrative and does not limit the disclosure. The various components including the blood pressure measurement controller 120 may be rearranged in other locations. Embodiments of the disclosure may work with any volume clamp method-based noninvasive finger arterial blood pressure measurement systems.

As will be described in more detail hereafter, finger cuff 104 in conjunction with blood pressure measurement controller 120 may include: a pump, a valve, a pressure sensor and control circuitry; may be utilized to measure the patient's blood pressure by monitoring the pressure of the bladder with the pressure sensor using the volume clamp method; and may display the patient's blood pressure on the patient monitoring device 130.

Figure 2:
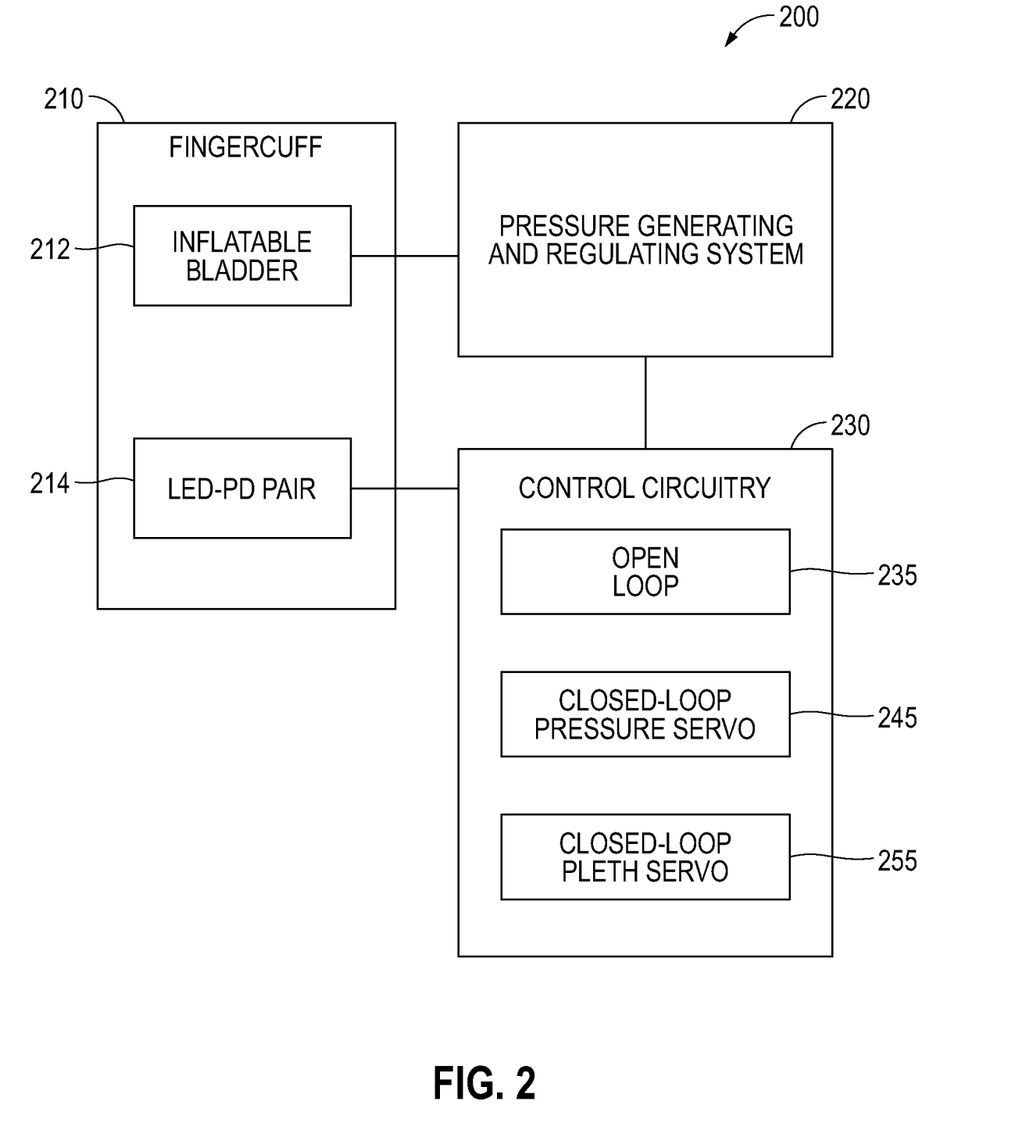
FIG. 2 is a block diagram illustrating an example environment in which embodiments of the disclosure may be practiced.

Referring to FIG. 2, a block diagram illustrating an example environment 200 in which embodiments of the disclosure may be practiced is shown. The finger cuff 210 may comprise an inflatable bladder 212 and an LED-PD pair 214. The inflatable bladder 212 may be pneumatically connected to a pressure generating and regulating system 220. The pressure generating and regulating system 220 may generate, measure, and regulate pneumatic pressure that inflates or deflates the bladder 212, and may comprise such elements as a pump, a valve, a sensor, and/or other suitable elements. When the bladder 212 is inflated, the finger cuff 210 may apply a pressure to the finger. The pressure applied to the finger by the finger cuff 210 may be the same as the pneumatic pressure in the bladder 212.

The finger cuff 210 may comprise a plethysmograph. The plethysmograph may make continuous volumetric measurements (or plethysmogram) of arterial blood flows within the finger. In one embodiment, the plethysmograph may comprise an LED-PD pair 214. The LED may be used to illuminate the finger skin and light absorption or reflection may be detected with the photodiode. Therefore, the plethysmogram may be generated based on the signal received from the photodiode.

The pressure generating and regulating system 220 and the LED-PD pair 214 may be connected to a control circuitry 230. The control circuitry 230 may instruct the pressure generating and regulating system 220 to inflate or deflate the bladder 212 based on a pressure setting, may receive pleth signals from the LED-PD pair 214, and may carry out necessary data manipulations. In particular, the control circuitry 230 may operate in one of three distinct modes: the open loop mode 235, the closed-loop pressure servo mode 245, and the closed-loop pleth servo mode 255. In an open loop mode 235, the control circuitry 230 may apply signals to the pressure generating and regulating system 220 and measure the resulting changes in pressure and/or pleth signals. In a closed-loop pressure servo mode 245, the control circuitry 230 may apply signals to the pressure generating and regulating system 220 in order to maintain a predetermined pressure value in the bladder 212, and measure the pleth signal response, which can be used to tune the pleth servo control loop gains. Moreover, in a closed-loop pleth servo mode 255, the control circuitry 230 may apply signals to the pressure generating and regulating system 220 in order to maintain a predetermined pleth value in the bladder, and measure the pressure signal, which can be used to determine the patient's blood pressure. The control circuitry 230 may be implemented in any suitable technologies including, but not limited to, proportional-integral-derivative (PID) controllers or other controllers. For example, the pneumatic pressure applied by the pump of the pressure generating and regulating system 220 to the bladder 212 of finger cuff 210 to replicate the patient's blood pressure based upon measuring the pleth signal received from the LED-PD pair 214 of the finger cuff 214 (e.g., to keep the pleth signal constant in the closed-loop pleth servo mode) and measuring the patient's blood pressure by monitoring the pressure of the bladder may be controlled by the control circuitry 230. However, other components of the blood pressure measurement controller 120 and/or other computing devices and/or the patient monitoring device 130 may implement functions of the volume clamping method.

Figure 3A:
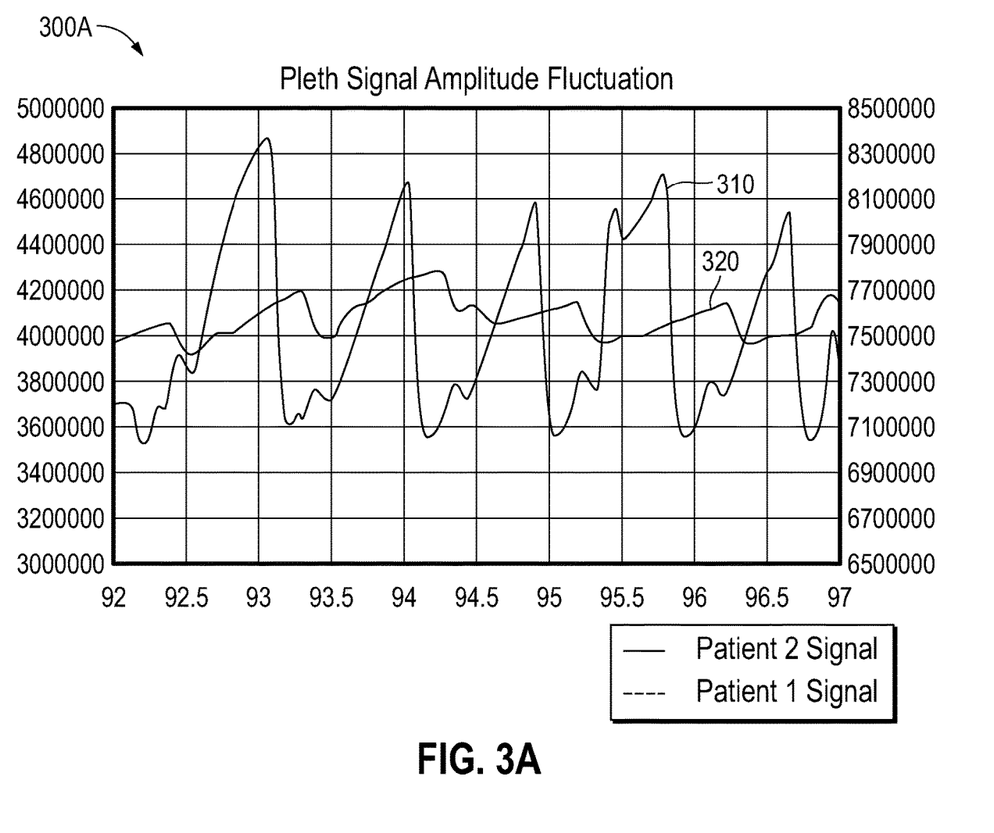
FIG. 3A is a diagram illustrating example plethysmograph signals corresponding to two different patients.

Referring to FIG. 3A, a diagram 300A illustrating example plethysmograph signals corresponding to two different patients is shown. A first plethysmograph signal 310 is measured from a first patient, and a second plethysmograph signal 320 is measured from a second patient.

Therefore, patients have different AC and DC characteristics to the pleth signal measured from their fingers. In particular, as illustrated in FIG. 3A, the first patient has large pulsatilities and his/her pleth signal has high AC magnitudes, whereas the pleth signal of the second patient has an AC component with a smaller pulsatile range. If a control system in the pleth servo mode is tuned to accommodate patients with large pulsatilities and high AC magnitudes in the pleth signal (e.g., the first patient), then the gains must be set to prevent oscillation at large pleth signal amplitudes. However, when the same control system with the same gains is used on a patient with a smaller pulsatile range for the AC component of the pleth signal (e.g., the second patient), then the control system will not respond as quickly or effectively as it did for the patient with large pulsatility, since it would appear that the pleth is much lower on the patient with low pulsatility.

The auto-tuning procedure, as will be described in more detail hereafter, allows the control circuitry, in the pleth servo mode, to adapt to the AC and DC characteristics measured from the patient's finger and tune the control circuitry to perform consistently and generate an accurate pressure waveform for patients with large and small pleth signal magnitudes.

Figure 3B:
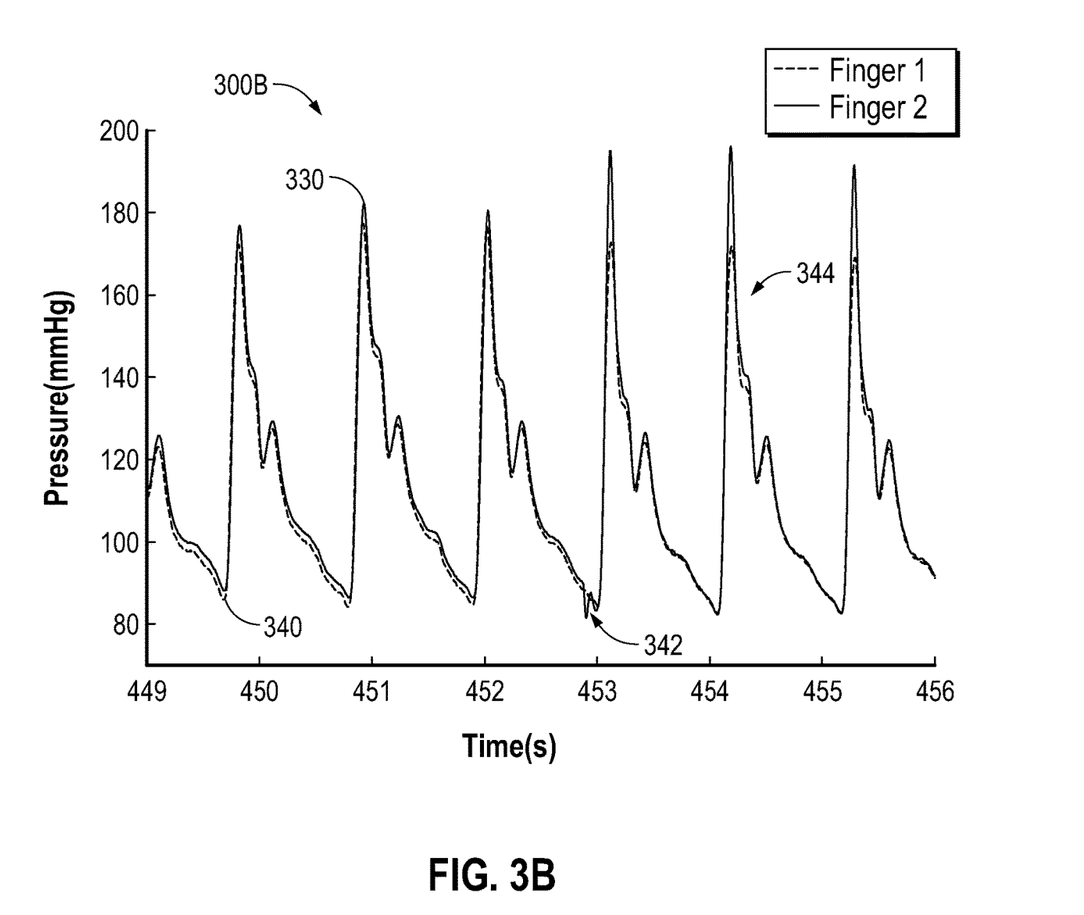
FIGS. 3B-3C are diagrams illustrating example pressure waveforms generated with control systems operating in the pleth servo mode on adjacent fingers of the same patient.
Figure 3C:
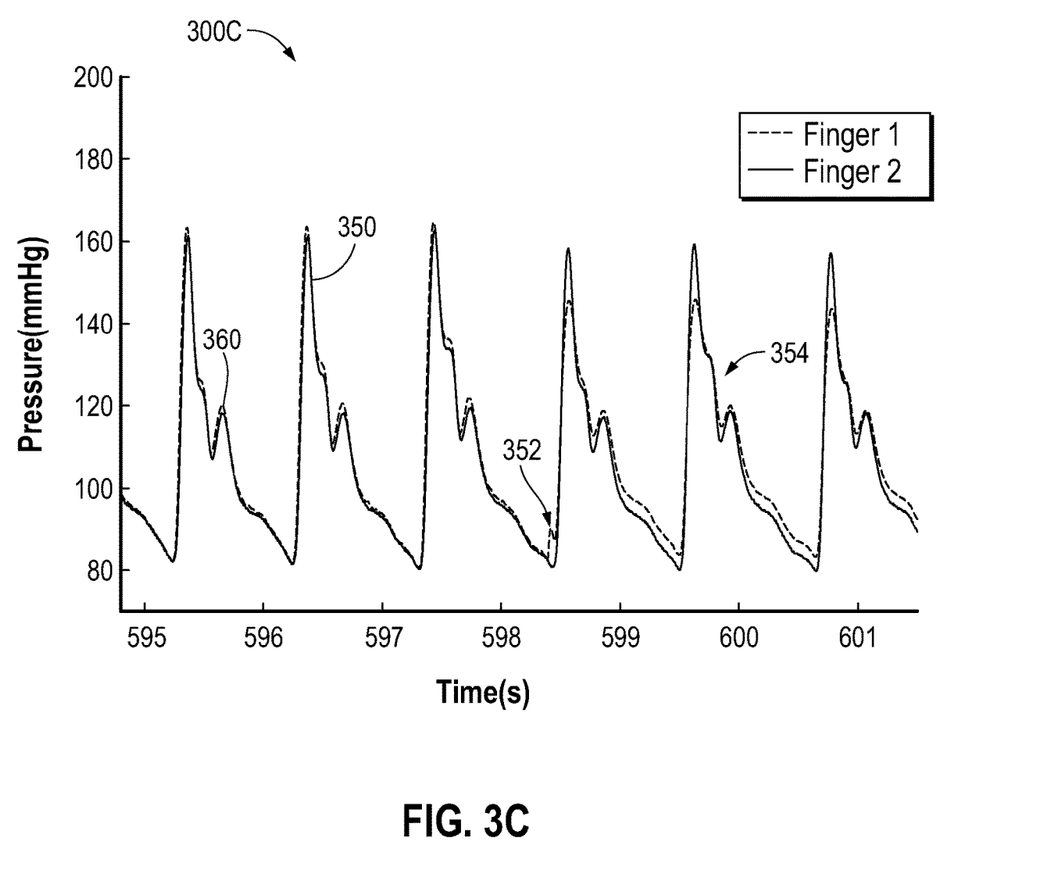

Referring to FIGS. 3B and 3C, diagrams 300B, 300C illustrating example blood pressure waveforms generated simultaneously on adjacent fingers of the same patient with control systems operating in the pleth servo mode are shown. In both figures a first blood pressure waveform 330, 350 is measured from a first finger using a first set of auto-tuned pleth servo gains, and a second blood pressure waveform 340, 360 is measured from a second finger using a second set of auto-tuned pleth servo gains. As can be seen, over the first three beats of each figure both blood pressure waveforms are closely matched indicating that both sets of pleth servo gains are well tuned and that the pressure signals are measured correctly.

Referring to the second three beats in FIG. 3B, the first set of auto-tuned pleth servo gains for the first finger are applied to the control system for the second finger. A small wrinkle 342 is visible in the second pressure waveform 340 when the transfer occurs. Following the switch in pleth servo gains on the second control system, the second control system operating in the pleth servo mode does not optimally control the pleth signal and measures the systolic blood pressure 344 erroneously high because the optimal pleth servo gains from the first finger are too large for the second finger.

Referring to the second three beats in FIG. 3C, the second set of auto-tuned pleth servo gains from the second finger are applied to the control system for the first finger. A small wrinkle 352 is visible in the first pressure waveform 350 when the transfer occurs. Following the switch in pleth servo gains on the first control system, the first control system operating in the pleth servo mode does not optimally control the pleth signal and measures the systolic blood pressure 354 erroneously low because the optimal pleth servo gains from the second finger are too small for the first finger.

Figure 4:
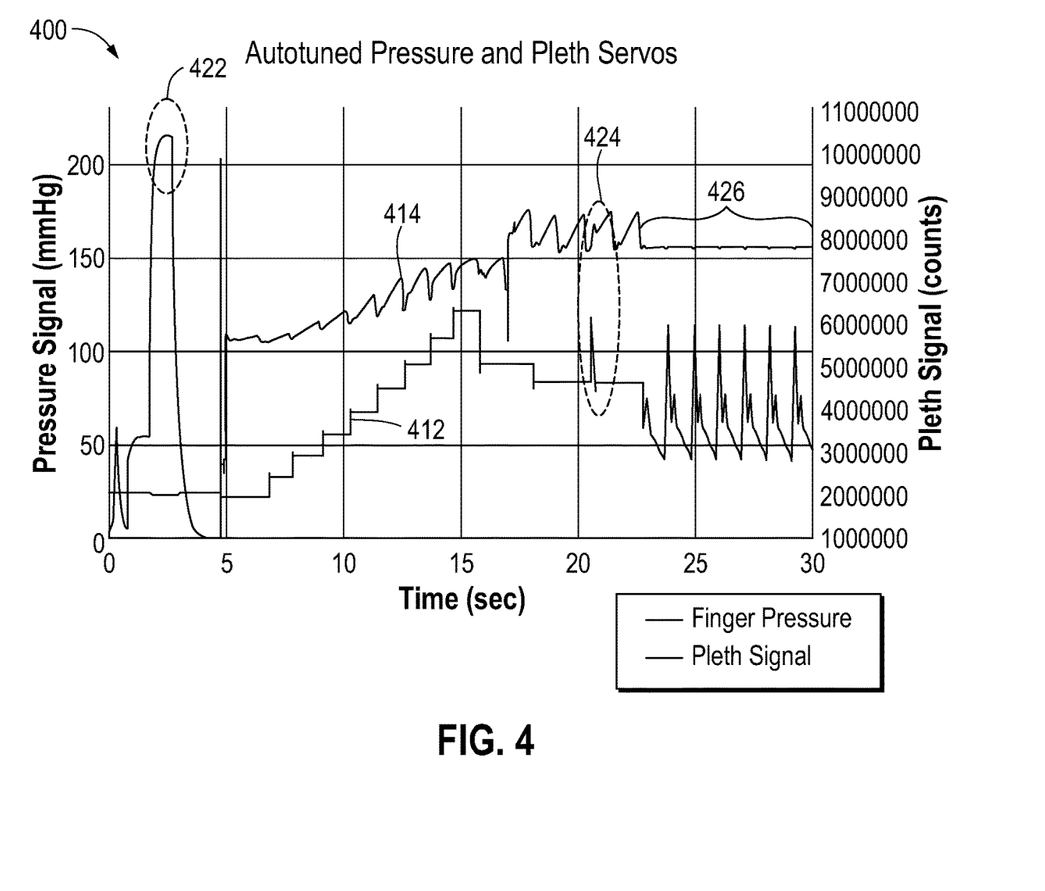
FIG. 4 is a diagram illustrating an example method for determining pressure servo and pleth servo gains, according to one embodiment of the invention.

Referring to FIG. 4, a diagram 400 illustrating an example method for determining pressure servo and pleth servo gains, according to one embodiment of the invention, is shown. The following operations are to be performed after the patient whose blood pressure is to be monitored has put the finger cuff on. A trace 412 illustrates the system pressure over time, and a trace 414 illustrates the pleth signal response over time. At a first region 422, a first open loop pressure impulse is applied and the pressure versus time response is monitored. The pressure versus time response is further illustrated as a trace 512 in FIG. 5A and as a trace 520 in FIG. 5B, as will be explained in more detail below. It should be appreciated that an open loop impulse and response refers to an impulse applied and a response measured when the control loop operation is paused (i.e., the control circuitry 230 is in the open loop mode). Based on the pressure versus time response, appropriate gains for the pressure servo mode can be determined (i.e., the pressure servo can be adaptively tuned based on the determined gains).

At a second region 424, while the control circuitry 230 is in the closed-loop pressure servo mode, a closed loop pressure impulse is applied using feedback to effect a controlled, predetermined pressure value in the cuff, and the pleth signal response is monitored. The pleth signal response is illustrated as a trace 532 in FIG. 5C and as a trace 540 in FIG. 5D, as will be explained in more detail below. It should be appreciated that a closed loop impulse and response refers to an impulse applied and a response measured when the control circuitry is operating in the closed-loop pressure servo mode. Based on the pleth signal response, appropriate gains for the pleth servo mode can be determined.

Thereafter, at a third region 426, an appropriate pressure waveform can be generated with the control circuitry operating in the closed-loop pleth servo mode tuned to the patient finger to measure the patient's blood pressure.

Figure 5A:
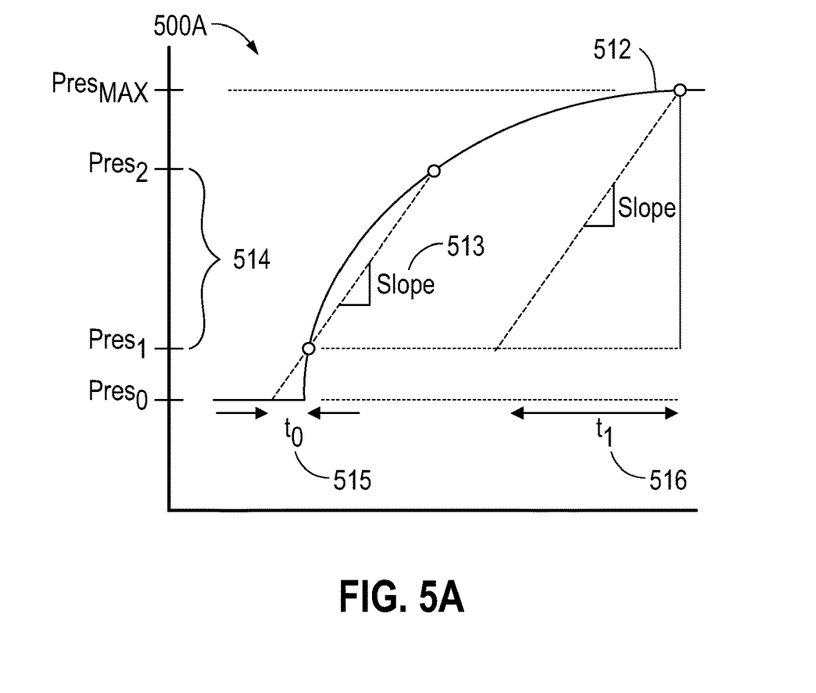
FIGS. 5A-5B are diagrams illustrating an example method for determining pressure servo gains, according to embodiments of the invention.
Figure 5B:
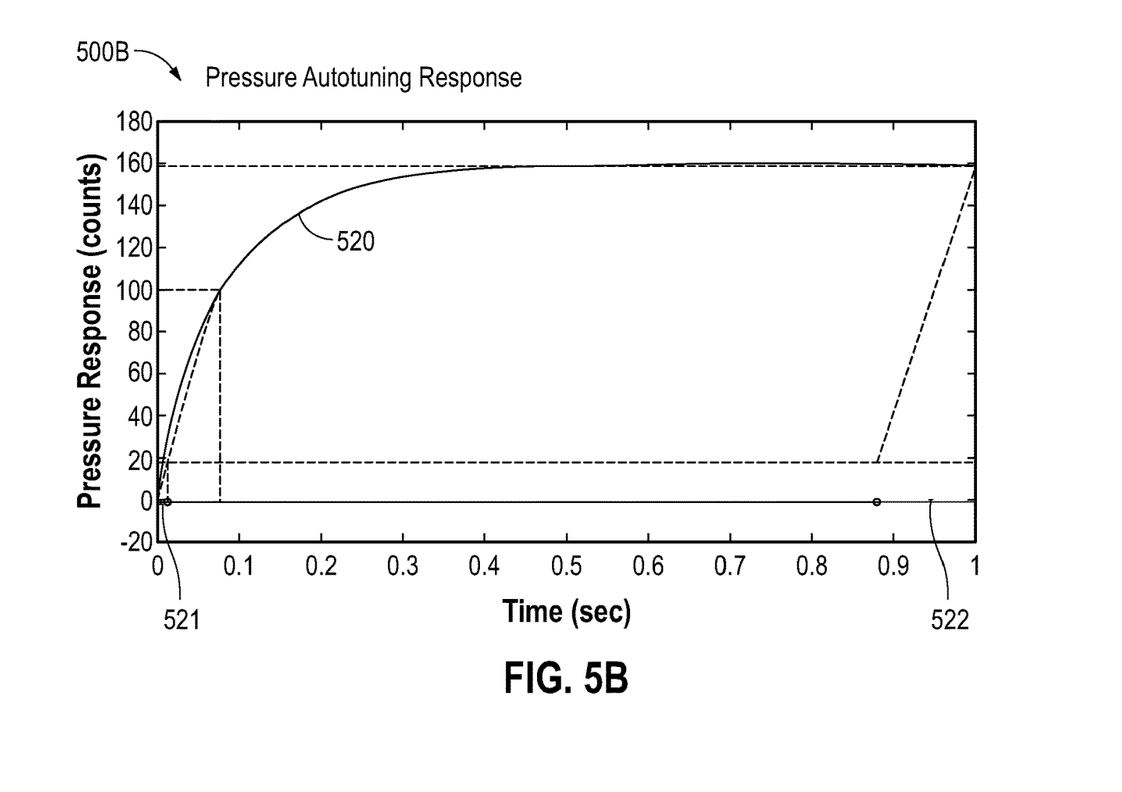

Referring to FIGS. 5A-5B, diagrams 500A-500B illustrating an example method for determining pressure servo gains, according to embodiments of the invention, are shown. As illustrated in FIG. 5A, the pressure signal trace 512 corresponds to the trace 412 in FIG. 4 at the first region 422. The pressure servo gains can be determined as a function of the dynamic response characteristics of the pressure signal trace 512. The response characteristics used to calculate the pressure servo gains may include: a turn-on delay period 515, the time rate of change of the pressure signal trace during one or more portions (subsets) of the response 513, the magnitude of the signal change during one or more portions (subsets) of the response 514, and the variation of the time rate of change and magnitude of signal change over multiple portions (subsets) of the response 516.

FIG. 5B illustrates another view of the pressure signal trace at the first region 422. In particular, the pressure signal trace 520 corresponds to the trace 412 in FIG. 4 at the first region 422. A first parameter 521 captures a turn-on delay and an effect of a rise slope, whereas a second parameter 522 captures the DC gain of the response and an effect of the rise slope. Therefore, the pressure servo gains can be determined based on the first parameter 521 and the second parameter 522. The first parameter 521 and second parameter 522 are time constants. In one embodiment, the pleth servo is a PID servo with four gains: a proportional gain, P, an integral gain I, a derivative gain, D, and a global gain, G, from which the pump drive signal is calculated. The PID gains may be calculated from the two time constants, first parameter 521, $T_1$, and second parameter 522, $T_2$, according to the following equations:

$$P = \frac{k_P \cdot T_2}{T_1} \quad \text{[Equation 1]}$$

$$I = \frac{k_I \cdot T_2}{(T_1)^2} \quad \text{[Equation 2]}$$

$$D = k_D \cdot T_2 \quad \text{[Equation 3]}$$

$$G = \frac{k_{GG}}{(P_2 - P_1)^{k_{GP}}} \quad \text{[Equation 4]}$$

where $k_P$, $k_I$, $k_D$, $k_{GG}$ and $k_{GP}$ are constants, and $P_1$ and $P_2$ are magnitudes of signal change 514 as shown in FIG. 5A.

In some embodiments, it may be advantageous to utilize different sets of constants $k_P$, $k_I$, $k_D$, $k_{GG}$ and $k_{GP}$. The sets of constants may be selected based upon various considerations including the mechanical configuration of the system such as the size of the cuff.

The methodology of calculating pressure servo PID coefficients from a pressure response as illustrated in FIG. 5A and Equations 1-4 can be applied to calculating pleth servo PID coefficients from a pleth response as well.

Figure 5C:
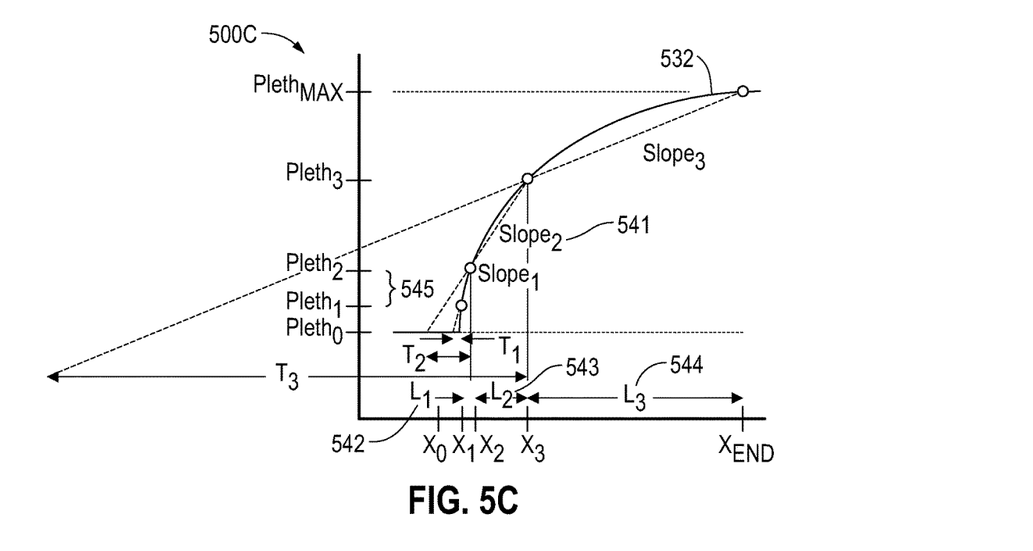
FIGS. 5C-5D are diagrams illustrating an example method for determining pleth servo gains, according to embodiments of the invention.
Figure 5D:
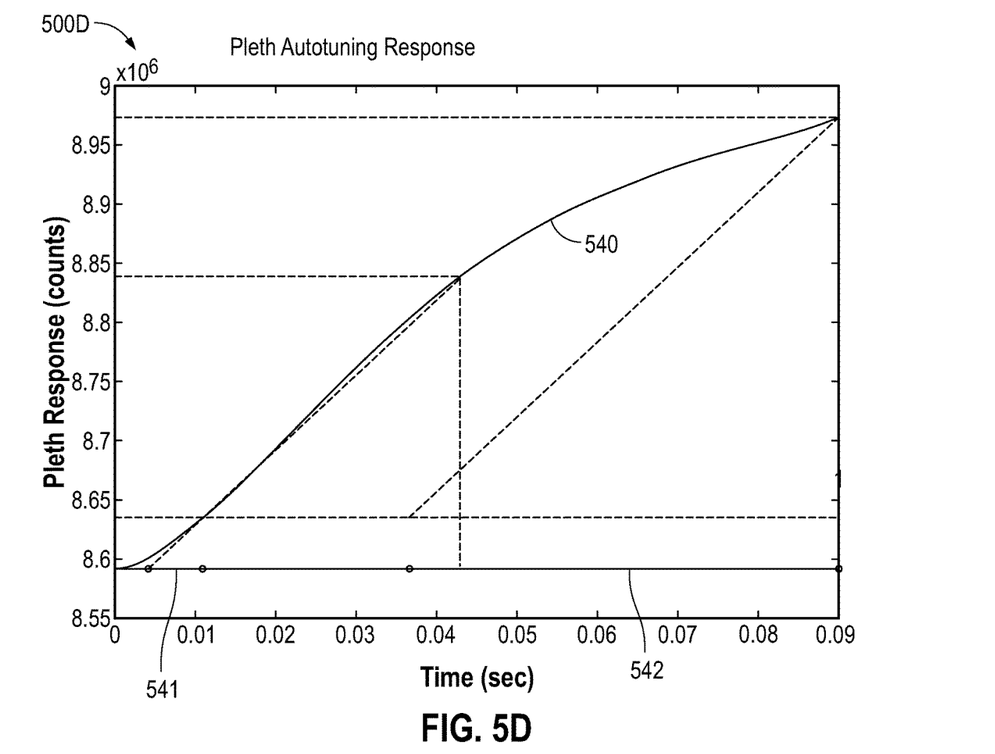

Referring to FIGS. 5C-5D, diagrams 500C-500D illustrating an alternate example method for determining pleth servo gains, according to embodiments of the invention, are shown. As illustrated in FIG. 5C, the pleth signal trace 532 corresponds to the trace 414 in FIG. 4 at the second region 424. The pleth servo gains can be determined as a function of the dynamic response characteristics of the pleth signal trace 532. The response characteristics used to calculate the pleth servo gains may include: a turn-on delay period, the time rate of change of the pleth signal trace during one or more portions (subsets) of the response, the magnitude of the signal change during one or more portions (subsets) of the response, and the variation of the time rate of change and magnitude of signal change over multiple portions (subsets) of the response.

FIG. 5D illustrates another view of the pleth signal trace at the second region 424. In particular, the pressure signal trace 540 corresponds to the trace 414 in FIG. 4 at the second region 424. A third parameter 541 captures a time rate of change of the pleth signal. A fourth 542, fifth 543 and sixth 544 parameters are time constants that capture time dynamics of fast, intermediate and slow changes. A seventh parameter 545 captures a magnitude of signal change. Therefore, the pleth servo gains can be determined based on the five parameters 541 (slope$_2$), 542 (L$_1$), 543 (L$_2$), 544 (L$_3$) and 545 (Pleth$_2$–Pleth$_1$). In one embodiment, the pleth servo is a PID servo with four gains: a proportional gain, P, an integral gain I, a derivative gain, D, and a global gain, G, from which the pump drive signal is calculated. The PID gains may be calculated from the five parameters 541, 542, 543, 544 and 545 according to the following equations:

$$P = k_P \cdot \text{slope}_2 \qquad \text{[Equation 5]}$$

$$I = k_I \cdot \text{slope}_2 \cdot (L_2 + L_3) \qquad \text{[Equation 6]}$$

$$D = k_D \cdot L_1 \qquad \text{[Equation 7]}$$

$$G = \frac{k_{GG}}{(Pleth_2 - Pleth_1)^{k_{GP}}} \qquad \text{[Equation 8]}$$

where $k_P$, $k_I$, $k_D$, $k_{GG}$ and $k_{GP}$ are constants, and Pleth$_1$ and Pleth$_2$ are magnitudes of signal change as shown in FIG. 5C.

In some embodiments, it may be advantageous to utilize different sets of constants $k_P$, $k_I$, $k_D$, $k_{GG}$ and $k_{GP}$. The sets of constants may be selected based upon various considerations including the mechanical configuration of the system such as the size of the cuff, the electrical configuration of the systems such as the drive signals into the LED or the gain settings of the PD amplifier, or aspects of the patient's physiology, such as the AC or DC pleth signals.

Figure 6A:
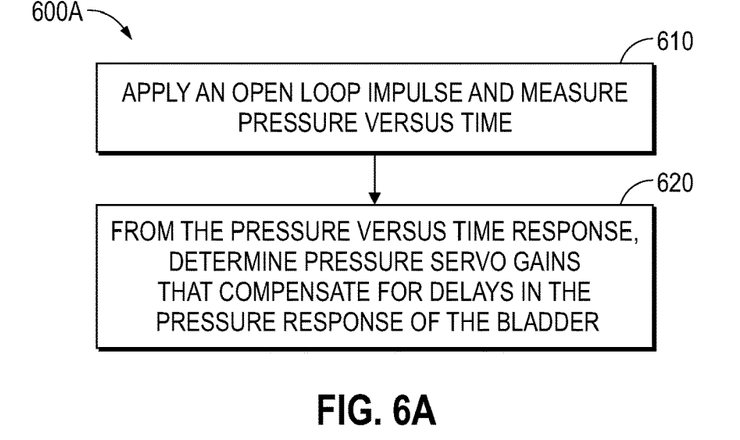
FIG. 6A is a flowchart illustrating an example method for tuning pressure servo gains, according to one embodiment of the invention.

Referring to FIG. 6A, a flowchart illustrating an example method 600A for tuning pressure servo gains, according to one embodiment of the invention, is shown. At block 610, an open loop pressure impulse may be applied and a pressure versus time response may be measured. At block 620, from the pressure versus time response, pressure servo gains that compensate for delays in a pressure response of the bladder 212 may be determined. The auto-tuning by the pressure servo system may further compensate for the actual application of the finger cuff to the patient's finger.

As has been described in detail, with reference to the previous figures and descriptions, the adaptive tuning system implemented with control circuitry may: apply an open loop pressure impulse and measures a pressure versus time response; and from the pressure versus time response, determine pressure servo gains that compensate for delays in a pressure response of the bladder 212. The auto-tuned pressure servo gains may be used in the pressure servo mode to further determine optimal pleth servo gains, and the pleth servo gains can be used in measuring the patient's blood pressure by the blood pressure measurement system utilizing the volume clamp method.

Figure 6B:
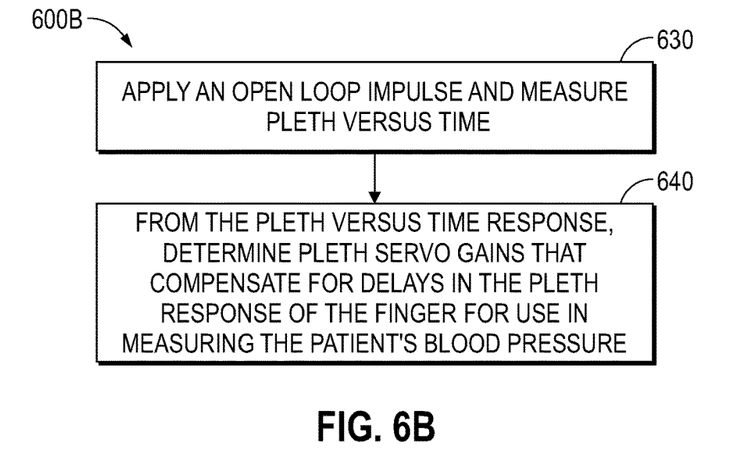
FIG. 6B is a flowchart illustrating an example method for tuning pleth servo gains, according to one embodiment of the invention.

Referring to FIG. 6B, a flowchart illustrating an example method 600B for tuning pleth servo gains, according to one embodiment of the invention, is shown. At block 630, an open loop pressure impulse may be applied and a pleth versus time response may be measured. At block 640, from the pleth versus time response, pleth servo gains that compensate for delays in a pleth response of the patient's finger for use in measuring the patient's blood pressure may be determined. The auto-tuning of the pleth servo gains may be to optimally interact with (e.g., accommodate) the physiology of the patient's finger, and may allow the control circuitry operating in the pleth servo mode to adapt to measured AC and DC characteristics of the pleth signal from the patient's finger and adjust for errors.

Figure 6C:
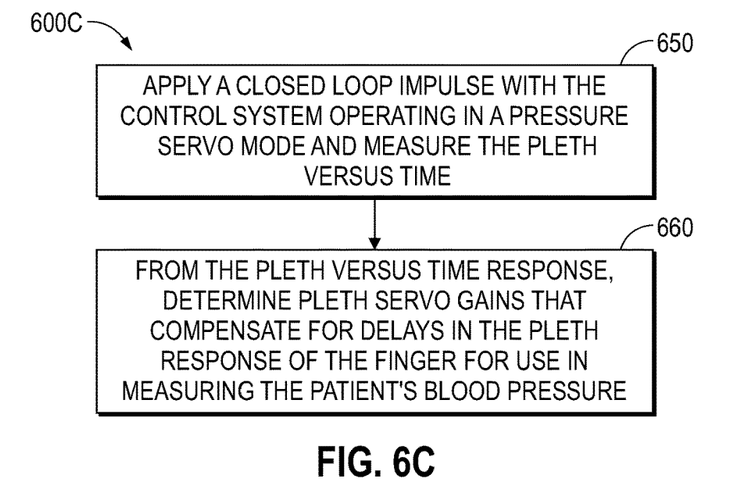
FIG. 6C is a flowchart illustrating an example method for tuning pleth servo gains, according to one embodiment of the invention.

Referring to FIG. 6C, a flowchart illustrating another example method 600C for tuning pleth servo gains, according to one embodiment of the invention, is shown. At block 650, a closed loop impulse may be applied when the control circuitry is operating in the pressure servo mode and a pleth signal response may be monitored. The pressure servo gains determined at block 620 may be applied to the control circuitry operating in the pressure servo mode. In other words, the closed loop pressure impulse may be applied in block 650 using pressure servo gains that have been auto-tuned according to the method 600A. At block 660, from the pleth signal response, pleth servo gains that compensate for delays in a pleth response of the patient's finger for use in measuring the patient's blood pressure may be determined. The viscoelastic response of the finger tissue and a blood flow of the artery may also be compensated for by the auto-tuning of the pleth servo gains. The auto-tuning of the pleth servo gains may be to optimally interact with (e.g., accommodate) the physiology of the patient's finger and may allow the control circuitry operating in the pleth servo mode to adapt to measured AC and DC characteristics of the pleth signal from the patient's finger and adjust for errors.

As has been described in detail, with reference to the previous figures and descriptions, the adaptive tuning system implemented with control circuitry may: apply a second closed loop impulse when the control circuitry is operating in the pressure servo mode and the pleth signal response is monitored; and from the pleth signal response, pleth servo gains that compensate for delays in a pleth response of the bladder 212 for use in measuring the patient's blood pressure may be determined. A viscoelastic response of the finger tissue and a blood flow of the artery may also be compensated for by the auto-tuning of the pleth servo gains. Based upon these functions, auto-tuning of the pleth servo gains may be applied to compensate for actual application of the finger cuff to the patient's finger. In particular, auto-tuning of the pleth servo gains may be applied to optimally interact with (e.g., accommodate) the physiology of the patient's finger. The auto-tuning of the pleth servo gains allows the control circuitry operating in the pleth servo mode to adapt to measured AC and DC characteristics of the pleth signal from the patient's finger and adjust for errors.

It should be appreciated that the auto-tuning of the pressure servo gains and the pleth servo gains may be repeated from time to time or periodically during operation to optimize patient blood pressure measurements.

Figure 7:
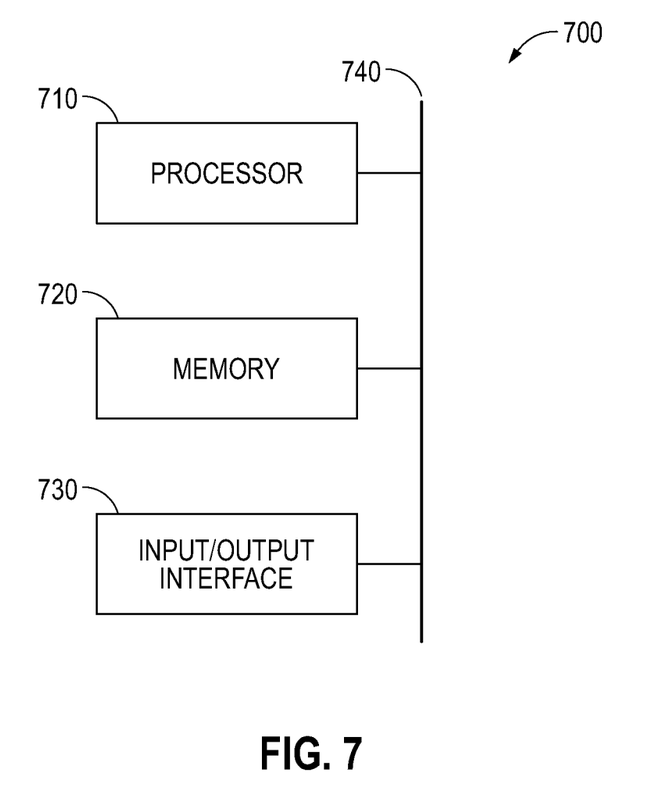
FIG. 7 is a block diagram illustrating an example control circuitry.

Referring to FIG. 7, a block diagram illustrating an example control circuitry 700 is shown. It should be appreciated that the control circuitry 700 represents a non-limiting example of a control circuitry 230 implementation. Other implementations (e.g., a PID controller) of the control circuitry 230 not shown in FIG. 7 are also possible. The control circuitry 700 may comprise a processor 710, a memory 720, and an input/output interface 730 connected with a bus 740. Under the control of the processor 710, data may be received from an external source through the input/output interface 730 and stored in the memory 720, and/or may be transmitted from the memory 720 to an external destination through the input/output interface 730. The processor 710 may process, add, remove, change, or otherwise manipulate data stored in the memory 720. Further, code may be stored in the memory 720. The code, when executed by the processor 710, may cause the processor 710 to perform operations relating to data manipulation and/or transmission and/or any other possible operations.

Therefore, embodiments of the disclosure provide a volume clamp-based blood pressure measurement system capable of adaptively auto-tuning its pressure servo gains and pleth servo gains. The auto-tuning of the pressure servo gains is based on a measured pressure versus time response to an open loop pressure impulse, and the auto-tuning of the pleth servo gains is based on a measured pleth signal response to either an open loop impulse or a closed loop impulse. The adaptive blood pressure measurement system described herein can accommodate a wide range of plethysmograph signals and finger mechanical responsivities.

In particular, adaptively tuning the pressure controller allows the system to: 1) accommodate a wide variation in cuff fit on the finger (e.g., variation in air volume within the pressurized bladder that interacts with the skin), 2) accommodate a wide variation in pump efficiency and flow capacity, and 3) achieve a consistent level of performance with a wide variation in finger properties (e.g., effective bulk modulus of tissue, blood volume variation and/or skin/callous thickness).

Further, adaptively tuning the pleth servo gains allows the volume clamp system to: 1) accommodate a wide range of blood volumes and variations in arterial to venous blood ratios, allowing the system to operate effectively on a larger patient population, and 2) accommodate a wider range of finger diameters, shapes and/or light absorption levels than possible with a static controller. Moreover, the system performance in response to physiological changes in the finger that could result from changes in the patient's physiology or hand position with respect to the heart level may be improved with adaptive tuning of the pleth servo gains.

It should be appreciated that adaptations may be made without deviating from the scope of the present invention. For example, alternate definitions of control gains with respect to measured step response may be used. As another example, the control system gains may be calculated as a function of pump command signal during operation. As yet another example, the control system gains may be calculated as a function of low-level oscillations on the pressure or plethysmograph signal during operation.

It should be appreciated that aspects of the invention previously described may be implemented in conjunction with the execution of instructions by processors, circuitry, controllers, control circuitry, etc. (e.g., processor 710 of FIG. 7). As an example, control circuitry may operate under the control of a program, algorithm, routine, or the execution of instructions to execute methods or processes (e.g., methods 600A-600C of FIGS. 6A-6C) in accordance with embodiments of the invention previously described. For example, such a program may be implemented in firmware or software (e.g. stored in memory and/or other locations) and may be implemented by processors, control circuitry, and/or other circuitry, these terms being utilized interchangeably. Further, it should be appreciated that the terms processor, microprocessor, circuitry, control circuitry, circuit board, controller, microcontroller, etc., refer to any type of logic or circuitry capable of executing logic, commands, instructions, software, firmware, functionality, etc., which may be utilized to execute embodiments of the invention.

The various illustrative logical blocks, processors, modules, and circuitry described in connection with the embodiments disclosed herein may be implemented or performed with a general purpose processor, a specialized processor, circuitry, a microcontroller, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor or any conventional processor, controller, microcontroller, circuitry, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module/firmware executed by a processor, or any combination thereof. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system to provide adaptive tuning through a control system to a finger cuff connectable to a patient's finger to be used in measuring the patient's blood pressure in the patient's artery by a blood pressure measurement system utilizing a volume clamp method, the finger cuff comprising:
   a light emitting diode (LED) and photodiode (PD) contained in the finger cuff to form an LED-PD pair to perform measurements of a pleth signal in the patient's artery in the volume clamp method implemented by the blood pressure measurement system; and
   a bladder to apply pressure to the patient's finger and the patient's artery, wherein, when the finger cuff is placed around the patient's finger, the bladder and the LED-PD pair aid in measuring the patient's blood pressure by the blood pressure measurement system utilizing the volume clamp method, wherein the adaptive tuning system:
   upon start-up, applies a first open-loop pressure impulse, to measure a pressure versus time response to determine pressure servo gains used in a pressure servo mode to compensate for delays in the pressure response of the bladder;

applies a second closed-loop pressure impulse in a closed-loop pressure servo mode and determines pleth servo gains that compensate for delays in a pleth response of the finger, wherein the pleth servo gains are determined based on dynamic response characteristics of the pleth signal to the second closed-loop pressure impulse; and uses the determined pleth servo gains from the second close-loop pressure impulse and the determined pressure servo gains from the first open-loop pressure impulse in the control system in a closed-loop pleth and pressure servo mode tuned to the patient's finger to maintain a predetermined pleth signal value in measuring the patient's blood pressure by the blood pressure measurement system utilizing the volume clamp method.

2. The system of claim 1, wherein the dynamic response characteristics comprise at least one of: a turn-on delay period, a time rate of change of a pleth signal trace during one or more portions of the response, a magnitude of signal change during one or more portions of the response, and a variation of the time rate of change or magnitude of signal change over multiple portions of the response.

3. The system of claim 1, wherein the determined pleth servo gains further compensate for a viscoelastic response of the patient's finger tissue and a blood flow of the artery.

4. The system of claim 1, wherein the determined pleth servo gains further allow the control system to adapt to measured AC and DC characteristics of the pleth signal from the patient's finger and adjust for errors.

5. The system of claim 4, wherein the determining the pleth servo gains is repeated periodically during operation.

6. The system of claim 1, wherein coefficients are used to determine the pleth servo gains from a first time and a second time, the coefficients being variable and dependent upon physiology of the patient.

7. The system of claim 6, wherein the coefficients are determined based upon measured AC and DC characteristics of the pleth signal from the patient's finger.

8. The system of claim 1, wherein the pressure servo gains are determined based on dynamic response characteristics of the pressure signal, the dynamic response characteristics comprising at least one of: a turn-on delay period, a time rate of change of a pressure signal trace during one or more portions of the response, a magnitude of signal change during one or more portions of the response, or a variation of the time rate of change or magnitude of signal change over multiple portions of the response.

9. The system of claim 8, wherein the determining the pressure servo gains is repeated periodically during operation to optimize patient blood pressure measurements.

10. The system of claim 8, wherein coefficients are used to determine the pressure servo gains from a first time and a second time, the coefficients being variable and dependent upon pressure system characteristics.

11. The system of claim 10, wherein the coefficients are determined based at least in part upon a size of the finger cuff bladder.

12. A method to provide adaptive tuning through a control system to a finger cuff connectable to a patient's finger to be used in measuring the patient's blood pressure in the patient's artery by a blood pressure measurement system utilizing a volume clamp method, the finger cuff comprising: a light emitting diode (LED) and photodiode (PD) contained in the finger cuff to form an LED-PD pair to perform measurements of a pleth signal in the patient's artery in the volume clamp method implemented by the blood pressure measurement system; and a bladder to apply pressure to the patient's finger and the patient's artery, wherein, when the finger cuff is placed around the patient's finger, the bladder and the LED-PD pair aid in measuring the patient's blood pressure by the blood pressure measurement system utilizing the volume clamp method, wherein, utilizing the control system the adaptive tuning method:

upon start-up, applies a first open-loop pressure impulse, to measure a pressure versus time response to determine pressure servo gains used in a pressure servo mode to compensate for delays in the pressure response of the bladder;

applies a second closed-loop pressure impulse in a closed-loop pressure servo mode and determines pleth servo gains that compensate for delays in a pleth response of the finger, wherein the pleth servo gains are determined based on dynamic response characteristics of the pleth signal to the second closed-loop pressure impulse; and uses the determined pleth servo gains from the second close-loop pressure impulse and the determined pressure servo gains from the first open-loop pressure impulse in the control system in a closed-loop pleth and pressure servo mode tuned to the patient's finger to maintain a predetermined pleth signal value in measuring the patient's blood pressure by the blood pressure measurement system utilizing the volume clamp method.

13. The method of claim 12, wherein the dynamic response characteristics comprise at least one of: a turn-on delay period, a time rate of change of a pleth signal trace during one or more portions of the response, a magnitude of signal change during one or more portions of the response, and a variation of the time rate of change or magnitude of signal change over multiple portions of the response.

14. The method of claim 12, wherein the determined pleth servo gains further compensate for a viscoelastic response of the patient's finger tissue and a blood flow of the artery.

15. The method of claim 12, wherein the determined pleth servo gains further allow the control system to adapt to measured AC and DC characteristics of the pleth signal from the patient's finger and adjust for errors.

16. The method of claim 15, wherein the determining the pleth servo gains is repeated periodically during operation.

17. The method of claim 12, wherein coefficients are used to determine the pleth servo gains from a first time and a second time, the coefficients being variable and dependent upon physiology of the patient.

18. The method of claim 17, wherein the coefficients are determined based upon measured AC and DC characteristics of the pleth signal from the patient's finger.

19. The method of claim 12, wherein the pressure servo gains are determined based on dynamic response characteristics of the pressure signal, the dynamic response characteristics comprising at least one of: a turn-on delay period, a time rate of change of a pressure signal trace during one or more portions of the response, a magnitude of signal change during one or more portions of the response, or a variation of the time rate of change or magnitude of signal change over multiple portions of the response.

20. The method of claim 19, wherein the determining the pressure servo gains is repeated periodically during operation to optimize patient blood pressure measurements.

21. The method of claim 19, wherein coefficients are used to determine the pressure servo gains from a first time and a second time, the coefficients being variable and dependent upon pressure system characteristics.

22. The method of claim 21, wherein the coefficients are determined based at least in part upon a size of the finger cuff bladder.

* * * * *